(12) United States Patent
Rakshit et al.

(10) Patent No.: US 10,710,954 B2
(45) Date of Patent: Jul. 14, 2020

(54) CONVERSION OF WOOD BASED HEMICELLULOSE PREHYDROLYSATE SUCCINIC ACID USING A HETEROGENEOUS ACID CATALAYST IN A BIPHASIC SYSTEM

(71) Applicant: Lakehead University, Thunder Bay (CA)

(72) Inventors: Sudip Kumar Rakshit, Thunder Bay (CA); Sai Swaroop Dalli, Thunder Bay (CA)

(*) Notice: Subject to any disclaimer, the term of this patent is extended or adjusted under 35 U.S.C. 154(b) by 0 days.

(21) Appl. No.: 16/225,185

(22) Filed: Dec. 19, 2018

(65) Prior Publication Data
US 2019/0382328 A1    Dec. 19, 2019

Related U.S. Application Data

(60) Provisional application No. 62/615,203, filed on Jan. 9, 2018.

(51) Int. Cl.
*C07C 51/31* (2006.01)
*B01J 39/05* (2017.01)
*B01J 39/20* (2006.01)

(52) U.S. Cl.
CPC .............. *C07C 51/31* (2013.01); *B01J 39/05* (2017.01); *B01J 39/20* (2013.01)

(58) Field of Classification Search
CPC ............ C07C 51/31; B01J 39/05; B01J 39/20
USPC ....................................................... 562/531
See application file for complete search history.

(56) References Cited

U.S. PATENT DOCUMENTS

2009/0234142 A1* 9/2009 Mascal ................ C07D 307/48
549/489

OTHER PUBLICATIONS

Choudhary et al., "Metal-free oxidative synthesis of succinic acid from biomass-derived furan compounds using a solid acid catalyst with hydrogen peroxide", Applied Catalyst, vol. 458, pp. 55-62. (Year: 2013).*

* cited by examiner

*Primary Examiner* — Deborah D Carr
(74) *Attorney, Agent, or Firm* — Michael R. Williams; Ryan W. Dupuis; Ade & Company Inc.

(57) ABSTRACT

A novel approach for the conversion of biomass based hemicellulose prehydrolysate to high value succinic acid has been investigated using a heterogeneous acid catalyst, Amberlyst 15 and hydrogen peroxide. A vital intermediate in this process, furfural, was oxidized in a biphasic system to produce succinic acid. Production of furfural in good yields is a limiting step in such processes for a number of reasons. Among the organic solvents evaluated, toluene was found to be an ideal solvent for furfural extraction and facilitated the conversion of furfural to succinic acid. Simultaneous extraction of furfural into the organic solvent as it is produced, increased the overall yield. It was observed that the developed method resulted in a succinic acid yield of 49% from the furfural obtained from hemicellulose prehydrolysate. It was found that 50 mg of Amberlyst 15 per mmole of furfural resulted in 100% FA conversion in less time.

12 Claims, 8 Drawing Sheets

Simultaneous production, separation and oxidation of furfural

CONVERSION OF WOOD BASED HEMICELLULOSE PREHYDROLYSATE SUCCINIC ACID USING A HETEROGENEOUS ACID CATALAYST IN A BIPHASIC SYSTEM

PRIOR APPLICATION INFORMATION

The instant application claims the benefit of U.S. Provisional Patent Application 62/615,203, filed Jan. 9, 2018.

BACKGROUND OF THE INVENTION

Succinic acid (SA) was identified by the Department of Energy, US,[1] as a platform chemical that will have a very high market in the near future. It plays a major role as a building block in synthesis of several polymers.[2-3] It has several applications in food, cosmetics, pharmaceuticals, biopolymers, polyesters, polyurethane, plasticizers and fine chemical industries:[4-5] In 2007, a market of 15 billion USD was projected for the chemicals which can be synthesized from succinic acid.[6] However, it has failed to reach such growth in production due to the high costs involved in its production. In 2015, the global production was 58.5 kilotons[7] and it is projected to reach 251.3 kilotons worth 701.0 million USD by 2022.[7]

Conventional industrial production of succinic acid involves the chemical conversion of maleic acid using heterogeneous metal catalysts like Pd/C and Zn/Hg.[4] Though the yields of SA are high, concerns on the use of petroleum based resources and expensive catalysts motivate researchers to look for alternative raw materials. Renewable substrates like agricultural and forest based residues have high potential for the production of succinic acid. However, its production from renewable lignocellulosic raw material is ,not carried out in industrial level due to the lack of cost effective processes to overcome low product yields. Studies indicate that the US, for example, produces approximately 1 billion tons of inedible biomass from forests and agricultural lands.[8] Therefore, several researchers are exploring alternate routes for the production of SA from low value substrates to reduce the overall production costs involved.

Microbial fermentation of various substrates like hexose, pentoses and glycerol using *Actinobacillus succinogenes*,[9] *Mannheimia succiniciproducensl*[10] and *Anaerobiospirillum succiniciproducens*[11] have been reported. Though fermentative yields are high, the downstream processing costs limit the use of these methods. For example, in Canada, BioAmber is one of the recently established industries for the production of biosuccinic acid. Other companies such as Riverdia, BASF—Corbion, Myriant and PTT MCC Biochem located at different parts of the world are also showing great interest in production of bio-succinic acid. However, its production is from corn starch[12] and not from inedible biomass like cellulose. Succinic acid produced from fermentation was estimated to cost 2.2 USD per kilogram with a production level of 5000 tons per year.[13] However, it has been projected that the price would drop to 0.55 USD if the production level increases to 75000 tons per year.[13] Alternative routes reported in literature for the production of succinic acid include the oxidation of 1,4-butanediol with nitric acid,[14] carbonylation of ethylene glycol, ethylene, acetylene, dioxane,[3] hydrogenation of fumaric acid in presence of Ru catalyst,[15] and condensation of acetonitrile to produce butanedinitrile which can be subsequently hydrolyzed to succinic acid.[16-17] Recent studies have shown that succinic acid can also be produced from furfural using a chemical conversion pathway without a metal catalyst,[18] for example, oxidation of levulinic acid using hydrogen peroxide.[19]

Choudhary et al. (2013) have reported that carboxylic acids like succinic acid can be synthesized from furan derivatives through the oxidative process using hydrogen peroxide in the presence of acid catalyst.[4] They have reported that Amberlyst-15 is an efficient replacement for the homogeneous acid catalyst in the oxidation of furans in water. Amberlyst-15 is a sulfonated polystyrene based ion-exchange resin with 4.7 mmol/g acidity.[20] It has a similar effect as sulfuric acid ($H_2SO_4$) in the synthesis of carboxylic acids from furan derivatives.[21] The heterogeneous catalyst, Amberlyst-15 has an advantage because it exists in solid phase and can be recycled easily for the oxidation reactions of furan derivatives like furfural, hydroxymethyl furfural, furoic acid etc. These furan derivatives are usually obtained from hexose and pentose sugars of edible and inedible crops. However, limited information is available in literature for the use of renewable resources such as hemicellulose prehydrolysate from agriculture or forest residue for the production of carboxylic acids such as succinic acid.

Xylose in hemicellulose can be converted to furfural which can then be converted to succinic acid. The major problem associated with the conversion of xylose to succinic acid is that furfural, an intermediate in this process, polymerizes and undergoes side reactions to form undesired products. It is important to avoid these side reactions during such conversions without loss in the substrate.

SUMMARY OF THE INVENTION

According to a first aspect of the invention, there is provided a method of synthesizing succinic acid comprising:

mixing a source of aqueous xylose with an organic solvent having low water solubility and a suitable acid to produce furfural; and mixing the furfural with hydrogen peroxide and a suitable catalyst to produce succinic acid.

The source of aqueous xylose may be a renewable source.

The synthesis of succinic acid may take place in a single vessel, for example, in one pot.

DESCRIPTION OF THE PREFERRED EMBODIMENTS

Figure 1:
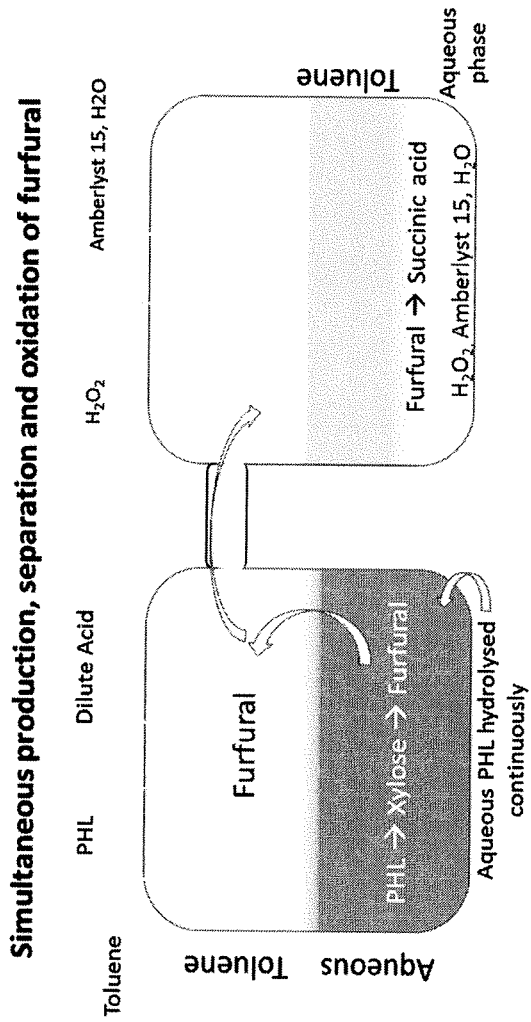
FIG. 1. Schematic representation of simultaneous production, separation and oxidation of furfural to produce succinic acid.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

The aim of this study was to avoid the side reactions and enhance the conversion of furfural to succinic acid in good yields. Conversion of hemicellulose prehydrolysate containing xylose to succinic acid with the use of a biphasic system is described herein.

As will be appreciated by one of skill in the art, hemicellulose streams contain substantial amounts of xylose. As discussed herein, xylose is a key reactant for the conversion. Commercially available xylose is purified and refined, making it expensive; However, hemicellulose contains 70-90% xylose which makes it a cheap source of xylose. However, it cannot be used for all reactions possible with xylose, because of the complex reactions caused by impurities present in the hemicellulose.

According to an aspect of the invention, there is provided a method of synthesizing succinic acid comprising mixing a source of aqueous xylose with an organic solvent having low water solubility and a suitable acid to produce furfural and then mixing the furfural with hydrogen peroxide and a suitable catalyst to produce succinic acid.

Specifically, as discussed herein, hemicellulose prehydrolysate was converted to succinic acid in a biphasic system using toluene as the organic solvent. The rate limiting step in this process, furfural production and separation, was optimized by determining ideal acid concentration (2%) and a good organic solvent (toluene) for extraction. The dilute sulfuric acid slows down the unwanted side reactions like furfural polymerization and toluene separates the furfural simultaneously. Oxidation of furfural in toluene was done using hydrogen peroxide (1:4 furfural/$H_2O_2$ mole ratio) and a heterogeneous acid catalyst, Amberlyst 15 (50 mg/mmol furfural). The molar yield of succinic acid obtained from furfural was found to be 49% in 24 h. The biphasic system facilitates simultaneous production, separation and oxidation of furfural to produce succinic acid. An advantage with the insolubility of succinic acid in toluene is that it provides easy separation after the reaction. This demonstrates the potential for the utilization of low value hemicellulose prehydrolysate to produce high value succinic acid.

As will be appreciated by one of skill in the art, any suitable source of hemicellulose may be used within the invention. For example, hemicellulose from sugarcane, rice husk, corn cob, wheat straw or the like from an agriculture residue or from forest residue can be used. While the specific chemical composition of hemicellulose varies according to the source and the growth conditions, all forms of hemicellulose share some components, for example, xylan, arabinan, mannan and glucan, although the components may exist in different linking patterns. Some examples and their percentages in the plant cell wall from which different hemicellulose sources are given the following table:

| Polymer components | Composition of polymers | Proportion in the cell wall (% w/w) |
| --- | --- | --- |
| Xylan | O-acetyl-4-O-methyl glucuronoxylan, and arabino-4-O-methyl glucuronoxylan | 10-35 |
| Glucuronoxylan | Glucuronic acid with D-xylopyranosyl | 20-30 |
| Glucurono-arabinoxylan | Glucuronic acid, Arabinose with Xylan | 10-25 |
| Glucomannan | Acetylated mannose and glucose | 2-5 |
| Xyloglucan | Glucan with xylose side chains | 20-25 |

As discussed above, any suitable organic solvent that has low water solubility may be used in the invention. However, in some embodiments, the preferred solvent is toluene. As discussed herein, among 8 solvents tested (ethanol, acetone, isopropyl alcohol, ethyl acetate, chloroform, petroleum ether, n-hexane and toluene) for the extraction of furfural, only ethyl acetate, chloroform and toluene were found to efficiently extract furfural from aqueous phase. While ethanol, acetone and isopropyl alcohol solubilize furfural in good proportions, these solvents are polar and miscible with aqueous phase. Hence with these solvents, the biphasic extraction of furfural is not possible.

The use of toluene for the extraction of furfural from aqueous phase was known previously. However, it was neither compared with the solvents listed above, nor used directly during the reaction, as herein. Rather, toluene was just listed as one of the organic solvents which can extract furfural from aqueous phase (Christensen et al. 1937; Haan et al. 2011). It was used to separate furfural along with other products like levulinic acid, formic acid from aqueous solutions (Thomas B. et al 2017). However, it is believed that simultaneous separation of furfural using toluene during the reaction has not been reported previously.

Preferably, the suitable catalyst is a macroreticular ion exchange catalyst having high acidic strength. In some embodiments, the catalyst Amberlyst 15™ (macro reticular polystyrene based ion exchange resin with strongly acidic sulfonic group) was chosen because of its macroreticular nature with high acid strength among heterogeneous acid catalysts. As will be apparent to one of skill in the art, other suitable catalysts may be used in the invention provided they have similar stability and efficiency as Amberlyst 15. However, only being pH dependent is not sufficient, as the ion exchange resin must be macroreticular in nature with equal or higher acidic strength compared to Amberlyst 15, for the product yields to be high. However, in other embodiments, where a lower yield is acceptable, similar but less suitable catalysts may be used within the invention.

For example, Amberlyst 732 has a similar acidic strength when compared to Amberlyst 15. However, unlike Amberlyst 15, it is not a macroreticular resin. The high number catalytic sites in Amberlyst 732 with similar acidic strength as Amberlyst 15, are packed densely and result in its microporous structure. Hence, the accessibility of catalytic sites by the substrate is lower in Amberlyst 732 than Amberlyst 15. However, the macroreticular structure of Amberlyst 15 resin make the catalytic sites more accessible to the substrate (furfural in this case) and results in better yields of product (succinic acid in this case).

Figure 8:
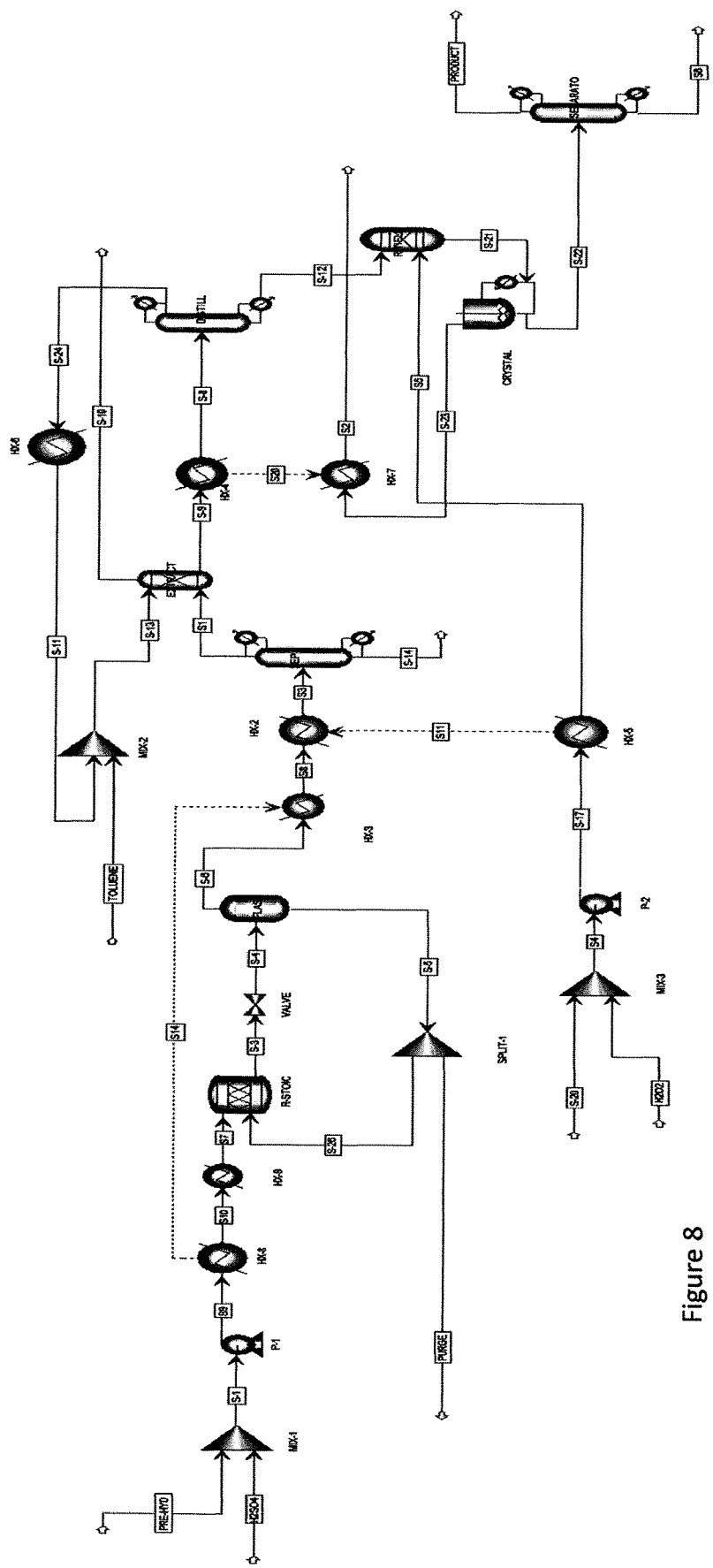
FIG. 8. Schematic design for the production of succinic acid from hemicellulose prehydrolysate using recycled Amberlyst 15 in biphasic system.

Amberlyst-15 has the benefits of ease of use, separation and recyclability for subsequent use. As discussed herein, the high solubility of the final product in the aqueous phase facilitated the recovery of the catalyst and reuse of the catalyst (FIG. 8). Specifically, the succinic acid yield was found to be increased for 2 cycles but was then subsequently reduced. Although the reaction media was stirred at a relatively low speed (100 rpm), the beads of the heterogeneous catalyst were found to break down and could not be used beyond the $3^{rd}$ recycle.

In addition to reusability, this solid catalyst offers mild acidic conditions compared to homogeneous acids (non-solid acids). Homogeneous acid catalysts must be diluted before addition to the reaction media due to their violent reaction with oxidizing agents in their concentrated forms. However, this was not observed with solid catalysts with acidic strength within the range reported.

In some embodiments of the invention, the succinic acid is purified following synthesis. As will be appreciated by one of skill in the art, the purification can be done by refrigeration or by another suitable technique known in the art, such as vacuum evaporation, freeze drying or the like.

Typically, furfural is separated after hydrolysing xylose using an acid. As discussed herein, this is normally done by steam distillation. However, it is a challenge to separate using this method beyond a certain limit. Also, at higher temperatures, furfural reacts with xylose or polymerizes itself to form humins (unwanted solid products). Furthermore, furfural and the aqueous phase forms an azeotropic mixture with a molar ratio of 1:1.85 at 96° C. For example, up to 35% of furfural may be lost in every batch.

The prior art teaches solvent extraction using some organic solvents. As described herein, several solvents can be used to separate furfural from the aqueous phase. However, there are two major bottlenecks in this process. I) During the separation of furfural, the organic solvent used to separate furfural partially dissolves in water, which traps furfural in the interface where organic solvent and aqueous phase coexist as single phase. Hence, furfural loss is directly dependent on the solubility of the organic solvent in water. As discussed herein, we determined that toluene has low solubility in water compared to the solvents used in this study and most of the organic solvents. II) Usually, solvent extraction is done after the xylose is hydrolyzed to furfural. Carrying out the hydrolysis reaction until all the xylose is converted is not feasible because the polymerization rate increases over time and there will be a huge loss of substrate (xylose) and product (furfural) in forming humins. Therefore, performing solvent extraction after the hydrolysis results in low amounts of furfural separation, as discussed herein.

To overcome the above-mentioned problems, we have developed a method to use the organic solvent (toluene) during the acid hydrolysis reaction which simultaneously separates furfural as it is produced. By this method, the polymerization reaction is avoided and the furfural is separated with an efficient organic solvent.

As will be appreciated by one of skill in the art, some separation methods such as gas stripping assisted vapor permeation (GSVP), adsorption on polymeric resins, pervaporation and the like are not viable at large scale separations. However, advantageously, our method prevents polymerization and the product formed is efficiently removed from the reaction phase, leading to higher production rates. Also, this one step reaction and extraction process reduces the number of steps involved in the process from two (reaction and subsequent separation) to one (simultaneous separation during reaction).

As will be apparent to one of skill in the art, the reaction in the absence of water will be very slow and limited. Specifically, water in the media allows the reaction to occur rapidly and dissolves the product, succinic acid. However, if too much water is added, the reaction will slow down due to the large interstitial space between reactants. Hence, the appropriate amount of water has to be added in order to dissolve the product completely.

According to an aspect of the invention, there is provided a method for succinic acid synthesis wherein:

Aqueous hemicellulose prehydrolysate and toluene in a ratio of 1:1 to 1:5 was added to a round bottomed flask at room temperature. This resulted in the formation of a two-phase system.

Sulfuric acid (1-5% w/w) was carefully added to the biphasic system with stirring. The round bottomed flask was attached to a reflux condenser and placed in an oil bath to maintain a temperature of 100° C. until all the xylose in the prehydrolysate is converted into furfural. This took approximately 4-6 h depending on the amount of substrate present.

The system was then cooled down to room temperature. The aqueous hydrolysate was removed from the biphasic system. The toluene phase was used further for the synthesis of succinic acid.

Furfural obtained from the previous step was oxidized to succinic acid using hydrogen peroxide in presence of Amberlyst 15. It is well known that the ratio of $H_2O_2$ to furfural is important. For example, studies on a range of ratios from 1:1 to 5:1 of $H_2O_2$ to furfural have indicated that 4:1 gives the best result. Accordingly, while a ratio of 1:1 to 5:1 may be used, for preferred results, a ratio of 4:1 should be used.

The stability of furfural is a key aspect in the above-mentioned reactions. In the first stage, where furfural is produced from xylose, furfural was separated from the reaction medium simultaneously with its production. In the second stage, toluene acts as a reservoir for furfural and the conversion occurs in the aqueous phase and does not affect furfural in toluene. Specifically, small amounts of furfural keep transferring from toluene to aqueous phase to reach equilibrium. However, as soon as furfural enters aqueous phase, it gets converted into succinic acid. Hence, furfural in this biphasic system never reaches equilibrium as the reaction is continuous. In both stages, furfural is separated within the reaction media which reduces the steps of the overall procedure and results in a new strategy for producing succinic acid from hemicellulose.

The invention will now be further explained by way of examples. However, the invention is not necessarily limited by the examples.

Characterization of the Hemicellulose Prehydrolysate Substrate (PHL)

The poplar hemicellulose prehydrolysate liquor (PHL) was obtained from a Canadian wood based industry where a novel two stage steam percolation pretreatment process was used in the extraction process.[22] The concentrated PHL supplied was stored in a freezer at −20° C. for future use. The composition of the PHL was analysed using HPLC to determine sugar and other components quantitatively (Table 1). The PHL contained some amount of furfural which was formed due to the high temperatures used during the pretreatment process.[23]

Succinic Acid Production

Traditionally, succinic acid is produced at large scale using either metal catalyzed conversion of maleic acid or fermentation of glucose. However, xylose obtained from the pretreatment of prehydrolysate also has considerable potential to be converted into succinic acid via furfural. Very few reports in literature discuss the conversion of furfural to succinic acid.[4,18,24] Succinic acid production from hemicellulose is challenging because of several constraints associated with acid hydrolysis of hemicellulose and the conversion of the intermediate, furfural, to byproducts. In this study, we first addressed the limitations of furfural yield due to the formation of byproducts like humins. Optimization of acid hydrolysis of hemicellulose prehydrolysate was done to determine the best conditions for high yields of furfural. We then compared a few organic solvents to determine an ideal solvent to separate furfural from the hydrolysate. By using these optimal conditions, a biphasic system was then developed to hydrolyze PHL to furfural and simultaneously separate furfural from the aqueous phase as soon as it is produced. Finally, the separated furfural was oxidized to SA using an efficient heterogeneous acid catalyst.

Optimization of Acid Hydrolysis of PHL

In the production of succinic acid from hemicellulose prehydrolysate, furfural plays an important role as the precursor of succinic acid. Hence, it is essential to produce furfural in good quantities which is subsequently converted to succinic acid. The polymeric form of xylose, xylan, in hemicellulose gets hydrolyzed in the presence of acid to produce xylose which in turn dehydrates to form furfural in the same reaction conditions. The reactions occur in the prehydrolysate during acid hydrolysis as shown in scheme 1.

Scheme 1. Set of reactions take place during acid hydrolysis of prehydrolysate.

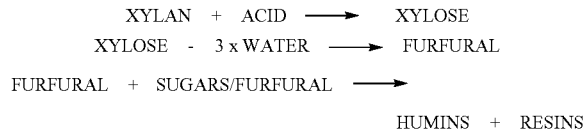

Various acid catalysts have been studied and discussed in the literature for the hydrolysis of biomass.[25-26] These reports indicate that sulfuric acid facilitates efficient hydrolysis. Therefore, it has been chosen to produce furfural from the hemicellulose prehydrolysate. Several processes and methodologies of acid hydrolysis have been invented and developed in the past and well discussed in literature.[27] Due to environmental concerns, it is always recommended to use dilute sulfuric acid at low dilutions. According to British Pharmacopoeia, any concentration below 10% (w/v) of sulfuric acid is considered as dilute.[28] We tried different acid concentrations under atmospheric and high pressure conditions in an autoclave at 121° C. and 15 psi pressure (Table 2). Low sulfuric acid concentrations as well as high acid concentrations yielded less furfural. Therefore, a range of acid concentrations were studied to determine optimum concentrations.

The hydrolysis of prehydrolysates using 1% sulfuric acid resulted in high xylose quantities but relatively low furfural. The activity of acid was not sufficient to hydrolyze the PHL and convert the xylose at the same time to produce furfural. Increasing the acid concentration resulted in higher furfural concentrations along with an increase in humins. However, in order to compare the effect of acidic strength, xylose to furfural and furfural to humins ratio were considered. In both the cases, 2% sulfuric acid has shown better results than other concentrations. The high xylose to furfural ratio is advantageous because the xylose produced in the hydrolysis can be hydrolyzed separately to produce furfural subsequently. On the other hand, in the case of high furfural to humin ratio, it is evident that low amounts of furfural were converted to humins during the hydrolysis.

The hydrolysis using 10% acid yielded very low amounts (1.28 g/L) of furfural and high amount (33.3 g/L) of humins. The yield of furfural from 10% acid hydrolysis was much lower than the hydrolyses using diluted concentrations. Therefore, it is evident that most of the furfural produced was converted to humins. However, some reports suggest that production of furfural is more efficient under pressure.[29] Therefore, we used an autoclave for the acid hydrolysis of prehydrolysate at 15 psi pressure and 121° C. temperature with 10% sulfuric acid. We observed that furfural concentration increased to 5.91 g/L with 33 g/L of humins compared to the experiments at atmospheric pressure. Even with 2% sulfuric acid, the humin formation was found to be relatively high. Though the acid hydrolysis under high pressure increases the yields of furfural, it also induces substantial humin formation. This results in significant furfural loss. Therefore, by performing the acid hydrolysis at atmospheric pressure, the polymerization of furfural can be slowed down and it is possible to obtain relatively higher levels of furfural.

For subsequent experiments, the acid concentration was lowered to 2% and hydrolysed the prehydrolysate under reflux. Under atmospheric pressure conditions, it resulted in lower amounts of humins (6.6 g/L) but high amounts of furfural (6 g/L). Therefore, it is evident that by decreasing the acid concentration, the furfural polymerization was suppressed. Due to the slow process of the side reaction, furfural was accumulated and resulted in good yields. These results were observed from the acid hydrolysis reactions which were carried out for 4 h. The xylose (96 g/L) obtained in the hydrolysis can be treated with acid repeatedly to convert it completely to furfural. However, continuous acid treatment is not recommended because after 5-6 h with this acid concentration, furfural was found to decrease due to the polymerization with xylose. Therefore, separating furfural from the aqueous solution of xylose after 4 h of acid hydrolysis is recommended to avoid polymerization reaction of furfural. Subsequently, the separated xylose can be hydrolysed again to produce more furfural.

Separation of Furfural from the Hydrolysed Prehydrolysate (Hydrolysate)

As described earlier, furfural is formed by the loss of 3 water molecules from xylose in the presence of acids. During this hydrolysis, a polymerization reaction causes loss of furfural by converting furfural into unwanted byproducts. One way to inhibit such reactions is to separate furfural from the aqueous media intermittently. Steam distillation is a common and widely used technique in industries to separate furfural from an aqueous phase. However, separation by such method is challenging as an azeotropic mixture is formed with 35% of furfural and 65% of water by weight in solution at 370 K under atmospheric pressure.[30] Therefore, it is difficult to separate all the furfural from the aqueous phase in this method.

Figure 2:
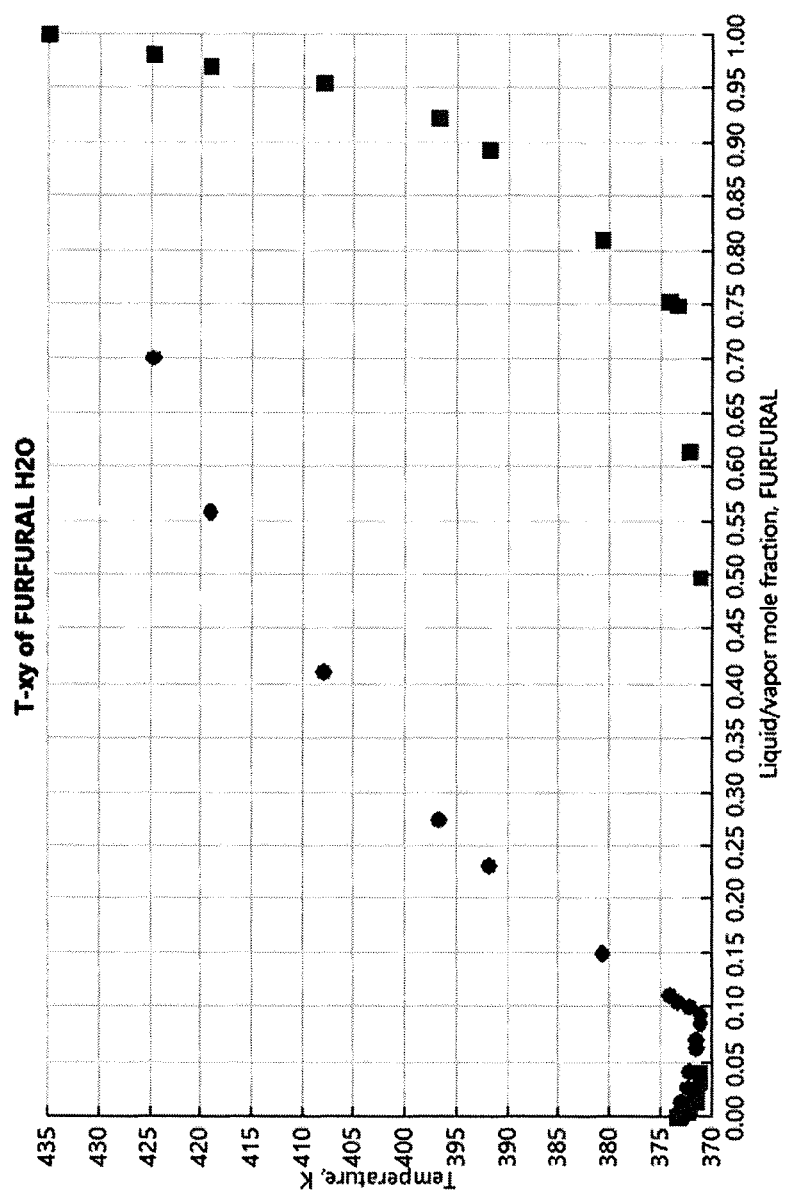
FIG. 2. Experimental T-xy diagram of furfural-water system at 1.01 bar

Other novel techniques are being explored to separate furfural from aqueous phase without any loss. Recently, Song et al (2015) reported a gas stripping assisted vapour permeation (GSVP) method and studied its energy efficiency.[31] Adsorption on polymeric resins,[32] pervaporation using hydroxy-terminated butadiene polyurethane membranes[33] and a patented technology using organic acids[34] are some of the recent developments in furfural separation. However, they are not feasible at large scale and the separation of furfural was found to be challenging as it forms an azeotropic mixture with water. A graphical representation of the effect of temperature on the furfural/water mixture is shown in FIG. 2. Specifically, as discussed herein, it was observed that water and furfural forms an azeotrope with 65% of mole fraction of water at 370 K. Therefore, separation of furfural would become almost impossible when its concentration reaches 35% of the aqueous solution at atmospheric pressure. However, two common techniques employed for azeotrope separations are 'pressure swing' and 'extractive distillation'. We have simulated the pressure swing distillation using Apen Plus software. The Non-Random Two-Liquid (NRTL) activity coefficient model was used to generate phase envelope diagrams at different pressures. It has been observed that the difference in azeotrope concentration with changing pressure was trivial. Therefore, the pressure swing operation would not be feasible in this case. For pressure swing to be feasible, it is recommended that a change of at least 5% of azeotropic composition must occur with the change in pressure.[35]

We chose to use an immiscible organic solvent having high furfural solubility that is capable of extracting furfural from aqueous phase. The use of such solvents provides an advantage of simultaneous separation of furfural during its formation. The biphasic reaction systems prevent side reactions like polymerization.[36] We have studied this method by determining a suitable solvent for furfural extraction. Several non-polar solvents were evaluated for their solubility of furfural and extractability from water. Simulation studies were also conducted using Aspen Plus software to determine the mutual solubility of organic phase, aqueous phase and furfural.

Solvent Determination to Extract Furfural

Figure 3:
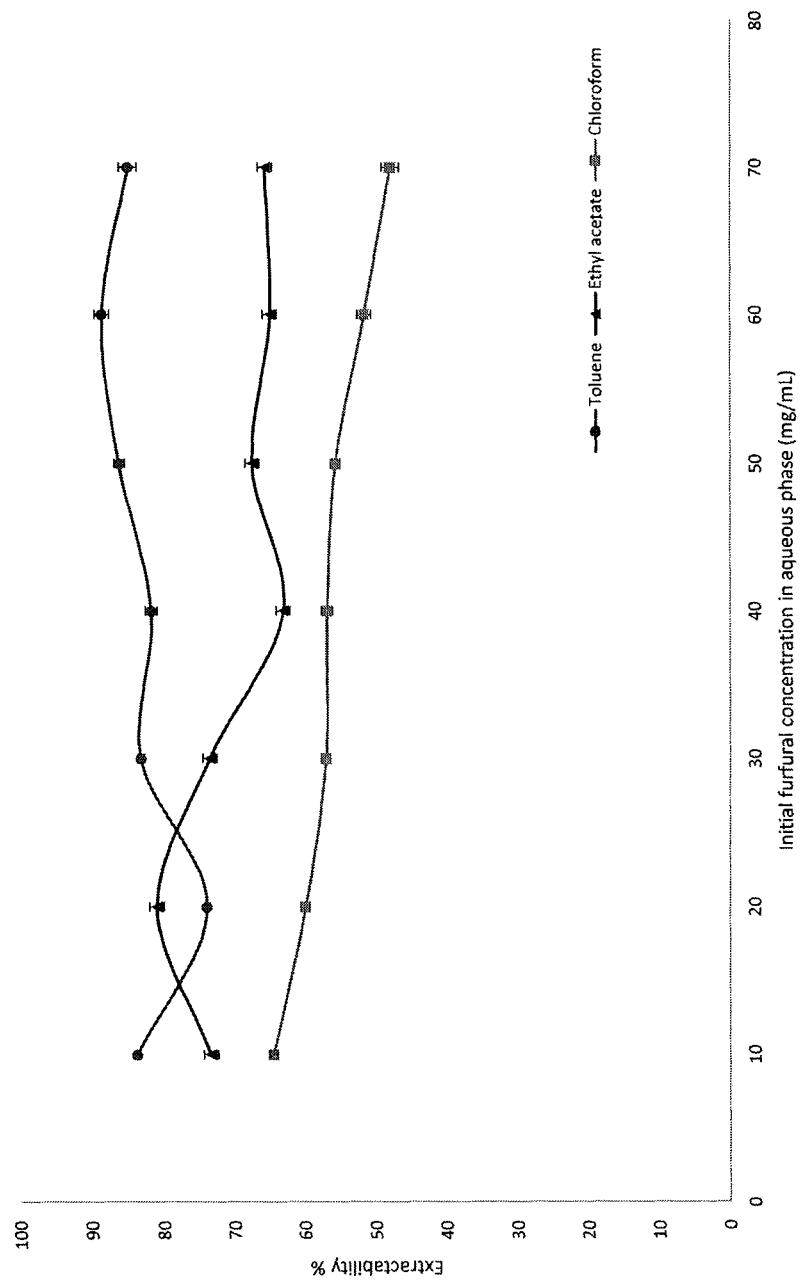
FIG. 3. Graphical representation of extractability of the organic solvents to extract from aqueous phase. The organic/aqueous ratio is 1:1.

A good organic solvent can substantially enhance the extraction of furfural from the aqueous phase without interfering in the reaction. For this purpose, three solvents, chloroform, ethylacetate and toluene were evaluated for the solubility and extractability of furfural from aqueous phase (FIG. 3). However, the extractability differs in each case. Three sets of aqueous furfural solutions were prepared with amounts ranging from 10 to 100 mg in water (1 mL). However, from the furfural solubility experiments, the maximum solubility of furfural in water was found to be 72-75 mg/mL. The vials with more than 7.5% of furfural resulted in two phases with the excess undissolved furfural.

The saturated aqueous solution with dissolved furfural was taken to examine the extractability of organic solvents. The organic solvents (1 mL) under study were added to the aqueous furfural solution. The final concentration of furfural in organic solvent after extraction was analyzed using a GC-FID. FIG. 3 shows the extractability (%) of the organic solvent, calculated from the concentrations of furfural in organic solvents obtained from GC results. From the FIG. 2 it is evident that toluene extracted 80-85% of furfural from aqueous phase at all concentrations. The extractability of the solvents was found to be in the order of toluene>Chloroform>Ethylacetate. However, 100% extraction of furfural was not observed in either case because of the mutual solubility of the solvents (water and organic solvent) present in the system resulting in a two-phase ternary system. From the graph (FIG. 2), it is evident that toluene extractability was almost constant with various furfural concentrations. However, other solvents seem to be losing their extractability. This can be attributed to the fact that with the change in concentrations of three components (organic solvent, water, furfural), at equilibrium, some of the organic solvent was lost to the aqueous phase and resulted in lower furfural concentration in the extractant organic phase.

Figure 4:
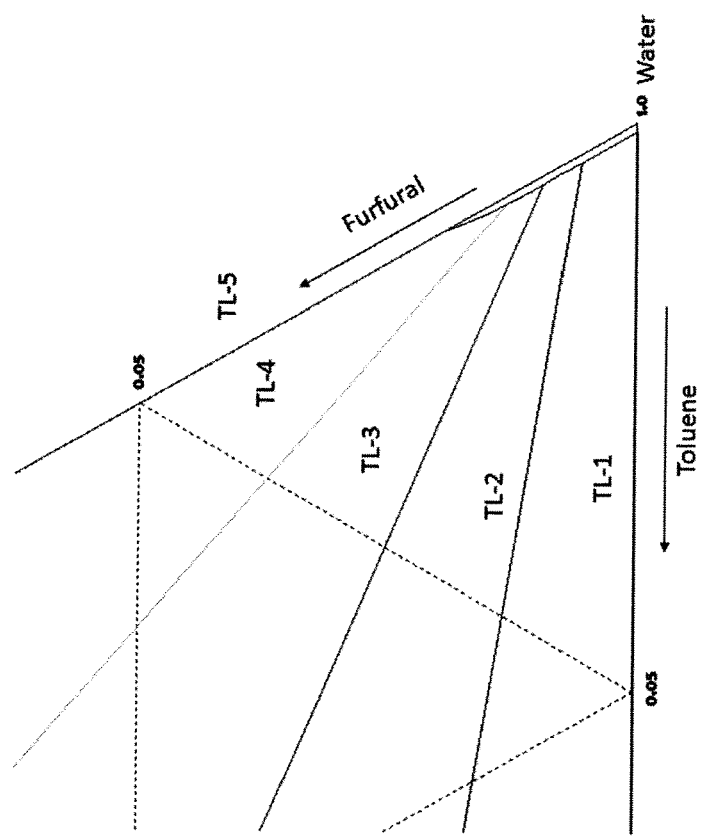
FIG. 4. a) Ternary diagram of liquid-liquid phase of toluene/water/furfural system simulation. b) Zoomed view of the solubility of toluene in water.
Figure 4:
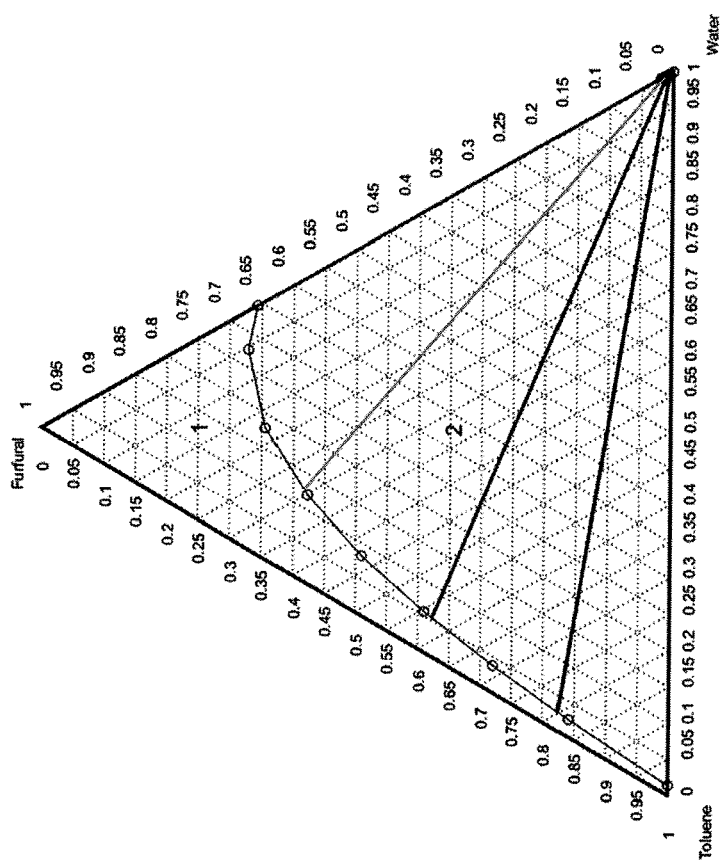
Figure 5:
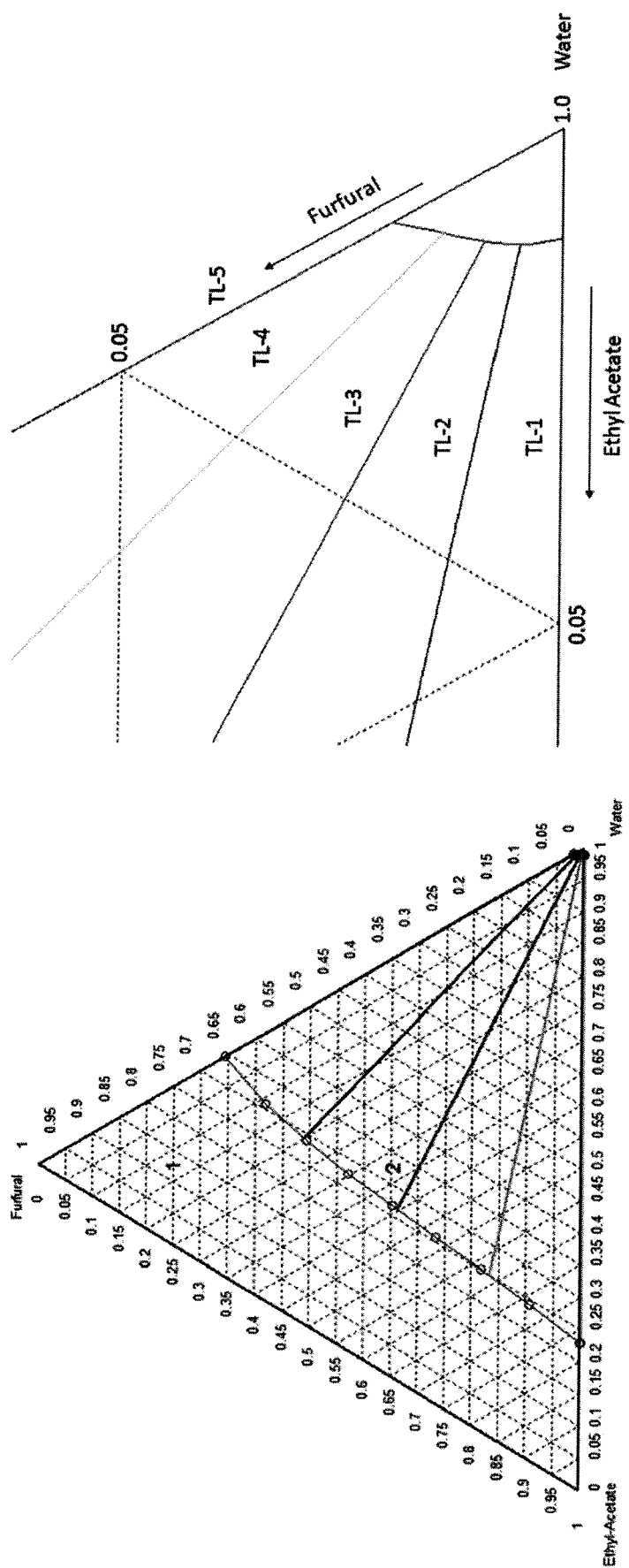
FIG. 5. a) Ternary Liquid-Liquid phase diagram of water/furfural/ethylacetate system. b) Zoomed view of the solubility of ethyl acetate in water.

The mutual solubility of the organic solvent and water was evaluated by plotting ternary diagrams using Aspen Plus software (version 8.4). Ethylacetate and toluene were found to solubilize furfural in high quantities. Therefore, they have been evaluated for their mutual solubility with water and furfural. Each ternary diagram (FIGS. 4 and 5) represents the mutual solubility of the aqueous, organic and furfural in the system. In both the ternary diagrams, the regions outside the envelop are single phase regions while the parts inside the envelop result in two phases with compositions at the end of the tie lines. The equilibrium solubility curves which form the envelop are shown in blue color and separates the two-phase regions from the single-phase regions. As examples, three tie lines which are connecting the two equilibrium solubility curves are shown in black, red, green and magenta colors. The vertices of the triangle represent pure components. The sides of triangle connecting any of two vertices represent mixture of two components. In the ternary diagrams, the left side of the triangle represents mixture of organic solvent and furfural in a single-phase region and illustrates organic layer and furfural are completely miscible in each other. The base of the triangle represents the miscibility of water and organic solvent. In FIG. 4a, it is clearly shown that water solubility in toluene phase is very low (~1%) whereas the solubility of toluene in water is also negligible (zoomed in FIG. 4b). However, in FIG. 5a, the solubility of water in ethyl acetate was found to be much higher (~22.5%) whereas ethylacetate was also slightly soluble in water which is relatively higher when compared to toluene (zoomed FIG. 5b).

From these data, it is found that water is less soluble in toluene than in ethyl acetate. Therefore, the use of toluene as an organic solvent was found to be the best for extraction of furfural from the aqueous phase and further used in this study.

Succinic Acid Synthesis Using Biphasic Sstem

From the above study, the optimum acid concentration (2% w/w) and toluene were used. The biphasic system formed by toluene and aqueous prehydrolysate helps in simultaneous furfural production and separation (FIG. 1). Subsequently, the separated furfural was converted to succinic acid in the toluene phase itself. The two stages, hemicellulose to furfural conversion and furfural to succinic acid conversion are discussed in the following sections.

Hemicellulose to Furfural in a Biphasic System

Xylose in aqueous prehydrolysate is converted into furfural with the help of an acid catalyst, sulfuric acid. In situ, sulfuric acid reacts with toluene used in the biphasic system and is converted to tosylic acid (Scheme 2) which was evident from the formation of a thick slurry immediately after addition of sulfuric acid to the biphasic system. However, hydrolysis is not affected because tosylic acid itself acts as a strong organic acid which is capable of carrying out the acid hydrolysis. Moreover, it was observed that when the reaction medium is heated to the required temperature, tosylic acid reverts back to toluene and sulfuric acid in presence of water and the biphasic system is reformed after 40-60 minutes of reaction. Therefore, hydrolysis of hemicellulosic xylan polymer is facilitated in the biphasic system along with simultaneous conversion of xylose to furfural in aqueous layer. Subsequently, furfural produced in the aqueous layer is rapidly transferred to the toluene layer. This was monitored by analyzing the reaction sample in GC-FID.

Scheme 2. Conversion of toluene to tosylic acid in presence of acid.

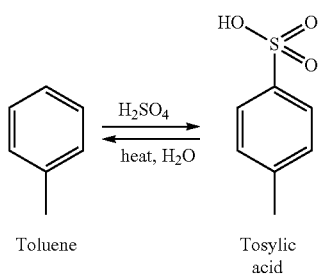

Toluene → Tosylic acid

Oxidation of Furfural to Succinic Acid

Furfural obtained from the previous step was oxidized to succinic acid using hydrogen peroxide in presence of Amberlyst 15. Choudhary et al. (2013) have studied the effect of various concentrations of hydrogen peroxide on the oxidation of furan derivatives.[18] In their study, the mole ratio of hydrogen peroxide to furfural required for high yields of carboxylic acids was reported to be 4:1. As higher or lower concentrations of hydrogen peroxide will result in low yields of succinic acid, a ratio of about 4:1 is described herein. Accordingly, in our study, we used the same ratio to obtain high yields of succinic acid; however, other ratios may be used within the invention.

An acid catalyst must be used with hydrogen peroxide to produce succinic acid. Hydrogen peroxide alone oxidizes the furfural present in aqueous phase and produces furoic acid. But, in presence of acid catalyst, hydrogen peroxide selectively yields succinic acid from furfural.[4] Sulfonic acid functional group on Amberlyst 15 is mainly responsible for succinic acid selectivity during the oxidation of furfural. Studies on the effect of various homogeneous acid catalysts like p-tosylic acid, hydrochloric acid, sulfuric acid, and heterogeneous acid catalysts like Amberlyst 15, Nafion NR50, Nafion SAC-13, γ-Al2O3, Nb2O5, ZrO2 has been reported elsewhere and can be used within the invention.[18]

Furfural in toluene phase was directly subjected to oxidation in presence of hydrogen peroxide and Amberlyst 15. However, this process takes place in the aqueous phase as hydrogen peroxide is miscible in water and immiscible in toluene. Therefore, addition of water to the toluene phase with furfural is necessary to facilitate the oxidation of furfural in presence of acid catalyst. A slight amount of water (10% V/V) is enough to solubilize succinic acid even as the yield reaches 100%. According to the Institute for Occupational Safety and Health of the German Social Accident Insurance database, the maximum solubility of succinic acid in water is 58 mg/mL at room temperature.[37] Therefore, we used 10 mL of water so that succinic acid is not saturated in the aqueous phase.

Though furfural selectively dissolves in toluene, it is also dissolved partially in water present in the system. Therefore, the partial amount of furfural dissolved in aqueous phase of the biphasic system gets oxidized to succinic acid. Due to the imbalance of furfural equilibrium in the two phases during the reaction, furfural tends to transfer into the aqueous phase continuously. Simultaneously, hydrogen peroxide in presence of the acid catalyst in the aqueous phase oxidizes the transferred furfural. The volumetric ratio of aqueous phase to toluene phase chosen for this reaction is ideal as total furfural (>99%) in toluene found to be transferred and converted. This was confirmed with GC analysis of the organic layer.

Figure 6:
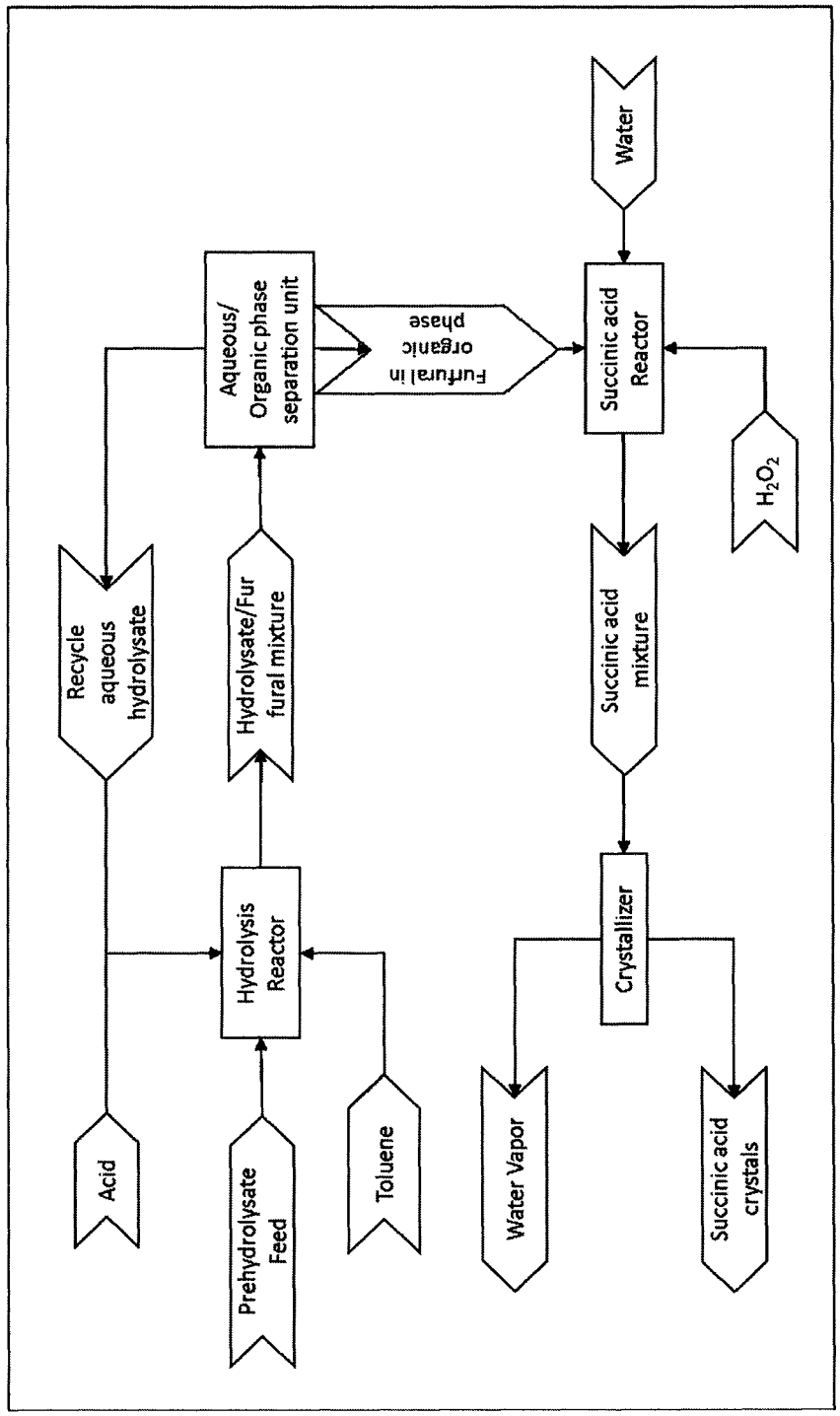
FIG. 6. Flow diagram of the proposed process of succinic acid production from hemicellulose prehydrolysate using biphasic system.

The reaction of furfural oxidation to succinic acid was monitored and few samples were taken during the reaction. Succinic acid is highly polar and insoluble in toluene. Therefore, the aqueous phase was analyzed for succinic acid content using HPLC whereas the toluene phase was analyzed using GC-FID for furfural content. The final yield of succinic acid from furfural was found to be 49.7% in 24 h. The overall reaction was shown in Scheme 3 and a schematic representation of the production process is given in FIG. 6. It was observed that in the biphasic system, the reaction was found to be faster and achieved good yields in less time. In this case, toluene acts as a reservoir for furfural and continuously supplies furfural to the aqueous phase where the oxidation takes place. Therefore, the biphasic system with toluene was found to be beneficial for production and synthesis of succinic acid from hemicellulose prehydrolysate.

Scheme 3. Overall reaction in the production of succinic acid from hemicellulose

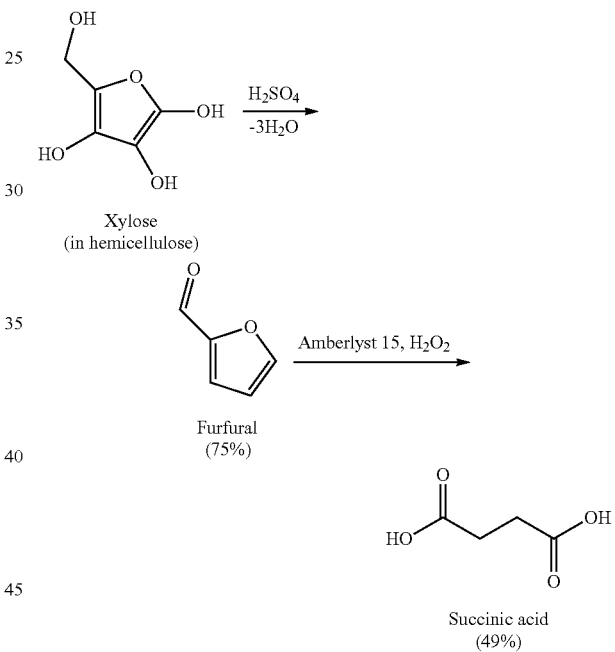

Effect of the Acid Catalyst Loading

Figure 7:
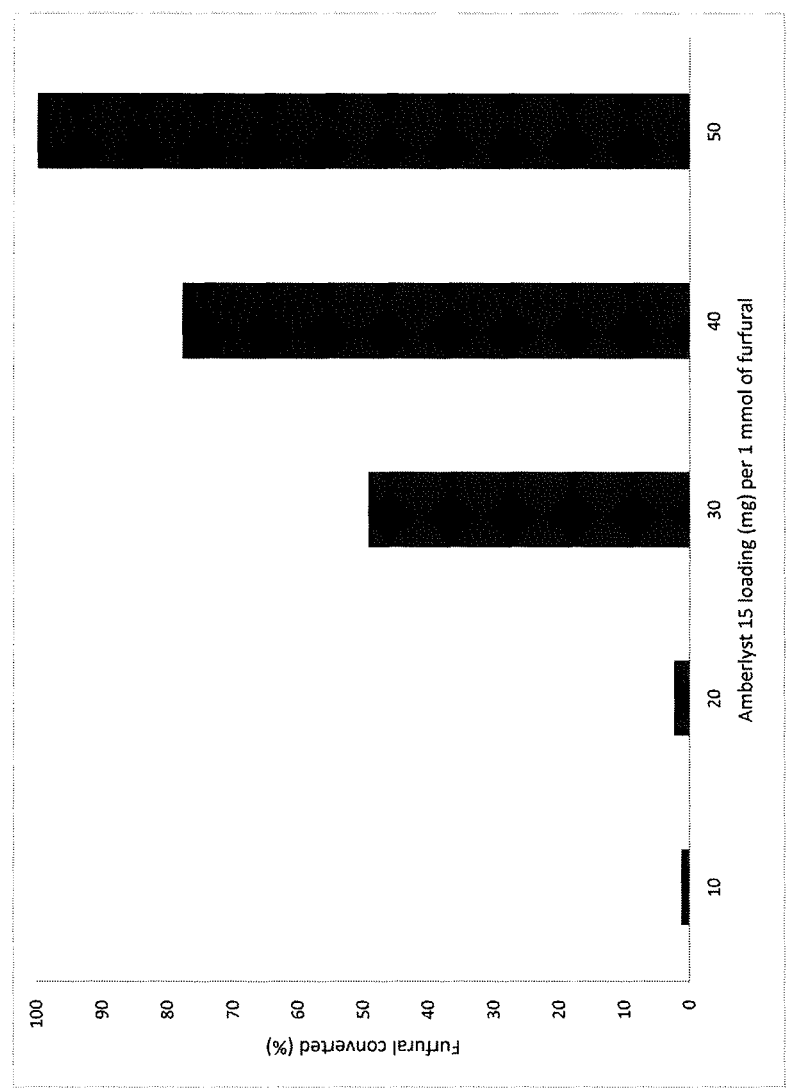
FIG. 7. Graphical representation of effect of catalyst loading in the oxidation of furfural at 4 hours of reaction time.

The effect of the amount of Amberlyst 15 in the reaction system was determined to study the variation in the yield of succinic acid and furfural conversion. A range of Amberlyst 15 catalyst amount (10-50 mg/ mmol furfural) were used to determine their effect on succinic acid synthesis. It was observed that in the first few hours of reaction, the furfural was converted into few intermediates which were subsequently succinic acid. From the FIG. 7, it is evident that 50 mg of Amberlyst 15 per each mmol of furfural was converting 100% of furfural within 4 h of reaction time. It shows that higher the catalyst loading, faster the conversion of furfural. Lower amounts of Amberlyst 15 were found to convert furfural much later than 50 mg of catalyst. Hence, 50 mg of Amberlyst was used to carry out the reaction to synthesize succinic acid from furfural in the biphasic system.

Analytical Techniques
HPLC

The composition of hemicellulose prehydrolysate, aqueous phases separated and the final product (succinic acid) were analyzed using an HPLC (Agilent Technologies 1260 Infinity) with Bio-Rad Aminex HPX-87H ion exclusion column (300 mm×7.8 mm) and a Refractive Index Detector (RID). The mobile phase used in this method was 5 mM $H_2SO_4$ with a flow rate of 0.5 mL/min at 50° C. The instrument was calibrated with standards of varying concentration and the response factor (RF) obtained for the standards was used to calculate the concentrations of the products formed.

GC-FID

Furfural in toluene was analyzed using a Thermo-scientific GC (Trace 1300 series) with Flame Ionization Detector (FID) and a capillary column (Trace Gold-TG-WAXMS A) (30 m length, 0.25 mm internal diameter, and 0.25 μm film thickness of cross linked polyethylene glycol). To detect furfural in less retention times using this system, a new method was developed by optimizing the gas flowrate and oven temperature. A ramped flow rate of the carrier gas was used with initial flow rate of 5 mL/min for 0.74 min and subsequently reduced and maintained at 4 mL/min until the end of the run. The temperatures of the oven and the detector were maintained at 200° C. and the inlet temperature was maintained at 250° C. Split mode (split flow: 200; split ratio: 40) injection was used in the analysis. Initially, the GC was calibrated with standards at different concentrations. Response factor (RF) of the standard furfural was obtained by the equation: [Peak area]=RF[standard concentration]. The obtained RF was used to determine the unknown concentration of furfural in the samples obtained during the reaction.

The analysis of furfural in toluene can be done by different methods using Gas Chromatography. However, to reduce the analysis time with the type of capillary column and detector, a new method was developed which optimized gas flow rates and oven temperature to obtain the eluent peaks with low retention times.

Materials and Methods
Substrate and Standards

Hemicellulose prehydrolysate was obtained from Green-Field Specialty Alcohols Inc., Canada. It was produced it from poplar wood chips using their proprietary pretreatment process.[22] Analytical grade furfural and succinic acid were purchased from Sigma Aldrich, whereas xylose, hydrogen peroxide, sulfuric acid and organic solvents namely toluene, ethylacetate, chloroform were purchased from Fisher Scientific. All the chemicals and solvents were used without further purification.

Experimental Procedure

The aqueous hemicellulose prehydrolysate (50 mL) was added to toluene (125 mL) in a round bottomed flask at room temperature resulting in a two-phase system. Sulfuric acid (2% w/w) was carefully added while the biphasic system was stirred. The round bottomed flask was attached to a reflux condenser and placed in an oil bath. The temperature of the oil bath was increased to maintain the temperature of the mixture at 100° C. and the mixture stirred until all the xylose in prehydrolysate is converted into furfural. The system was then cooled down to room temperature. The aqueous hydrolysate was separated out from toluene phase. The toluene solution was then separated and used for the synthesis of succinic acid. The aqueous layer containing unconverted xylose was hydrolysed again until all the xylose present was converted.

The toluene phase obtained was added to a mixture of 10% (v/v) deionized water, Amberlyst 15 (50 mg) and hydrogen peroxide (4 mmole) in another round bottomed flask. The temperature was then increased to 80° C. and maintained for 24 h. The whole reaction process is shown in the FIG. 1. After the reaction, the aqueous layer and the catalyst, Amberlyst 15 were separated from the organic phase. The toluene phase was analyzed for the residual furfural using a GC-FID. Once most of the furfural in toluene was converted, it was distilled to obtain relatively pure toluene and reused for subsequent batches of experiments. The aqueous layer was concentrated in a rotary evaporator and filtered to remove undissolved particles. The resultant solution was kept in a refrigerator to crystallize out the succinic acid. The crystallized product was analyzed using an HPLC to confirm the product was succinic acid.

The scope of the claims should not be limited by the preferred embodiments set forth in the examples but should be given the broadest interpretation consistent with the description as a whole.

REFERENCES

1. Werpy, T.; Peterson, G. Top value added chemicals from biomass; Energy Efficiency and Renewable energy: US, 2004; pp 1-76.
2. Werpy, T.; Petersen, G.; Aden, A.; Bozell, J.; Holladay, J.; White, J.; Manheim, A.; Eliot, D.; Lasure, L.; Jones, S. Top value added chemicals from biomass. Volume 1-Results of screening for potential candidates from sugars and synthesis gas; DTIC Document: 2004.
3. Pinazo, J. M.; Domine, M. E.; Parvulescu, V.; Petru, F., Sustainability metrics for succinic acid production: A comparison between biomass-based and petrochemical routes. Catalysis Today 2015, 239, 17-24.
4. Choudhary, H.; Nishimura, S.; Ebitani, K., Metal-free oxidative synthesis of succinic acid from biomass-derived furan compounds using a solid acid catalyst with hydrogen peroxide. Applied Catalysis A: General 2013, 458, 55-62.
5. Tachibana, Y.; Masuda, T.; Funabashi, M.; Kunioka, M., Chemical Synthesis of Fully Biomass-Based Poly(butylene succinate) from Inedible-Biomass-Based Furfural and Evaluation of Its Biomass Carbon Ratio. Biomacromolecules 2010, 11 (10), 2760-2765.
6. McKinlay, J. B.; Vieille, C.; Zeikus, J. G., Prospects for a bio-based succinate industry. Appl Microbiol Biotechnol 2007, 76 (4), 727-40.
7. MarketsandMarkets, Succinic Acid Market by Type (Bio-based, Petro-based), Application (Polyurethane, Resins, Coatings & Pigments, Pharmaceuticals, Plasticizers, Food & Beverage, PBS/PBST, Solvents & Lubricants, De-Icer Solutions, Personal Care, and Others), and by Region-Global Forecast to 2021. 2016.
8. Wright, L.; Boundy, B.; Perlack, B.; Davis, S.; Saulsbury, B., Biomass Energy Databook. 1 ed.; Energy Efficiency and Renewable Energy, Department of Energy: Oakridge National Laboratory, Tenessee, 2006.
9. Salvachúa, D.; Mohagheghi, A.; Smith, H.; Bradfield, M. F. A.; Nicol, W.; Black, A. B.; Biddy, M. J.; Dowe, N.; Beckham, G. T., Succinic acid production on xylose-enriched biorefinery streams by *Actinobacillus succinogenes* in batch fermentation. Biotechnology for Biofuels 2016, 9 (1), 1-15.
10. Lee, P. C.; Lee, S. Y.; Hong, S. H.; Chang, H. N., Batch and continuous cultures of *Mannheimia succiniciprod-* ucens MBEL55E for the production of succinic acid from whey and corn steep liquor. Bioprocess Biosyst Eng 2003, 26 (1), 63-67.
11. Lee, P.; Lee, S.; Chang, H., Kinetic study on succinic acid and acetic acid formation during continuous cultures of *Anaerobiospirillum succiniciproducens* grown on glycerol. Bioprocess Biosyst Eng 2010, 33 (4), 465-471.
12. BioAmber Technology: Innovation that drives the emergence of greener chemistry. hftp://www.bio-amber.com/bioamber/en/technology#conversion_technology (accessed Mar.23).
13. Kang, S. H.; Chang, Y. K., Removal of organic acid salts from simulated fermentation broth containing succinate by nanofiltration. Journal of Membrane Science 2005, 246 (1), 49-57.
14. Svetlakov, N.; Nikitin, V.; Orekhova, A., Oxidation of Tetrahydrofuran and 1,4-Butanediol with Nitric Acid. Russian Journal of Applied Chemistry 2002, 75 (4), 669.
15. Rosi, L.; Frediani, M.; Frediani, P., Isotopomeric diols by "one-pot" Ru-catalyzed homogeneous hydrogenation of dicarboxylic acids. Journal of Organometallic Chemistry 2010, 695 (9), 1314-1322.
16. AnhuiSunsingChemicals Succinic acid factory. http://product.lookchem.com/item/7510/Succinic-Acid-factory.html (accessed Feb 28).
17. Ayers, G. W.; Fierce, W. L., Synthesis of succinonitriles. Google Patents: 1957.
18. Hemant, C.; Shun, N.; Kohki, E., Highly Efficient Aqueous Oxidation of Furfural to Succinic Acid Using Reusable Heterogeneous Acid Catalyst with Hydrogen Peroxide. Chemistry Letters 2012, 41 (4), 409-411.
19. Dutta, S.; Wu, L.; Mascal, M., Efficient, metal-free production of succinic acid by oxidation of biomass-derived levulinic acid with hydrogen peroxide. Green Chemistry 2015, 17 (4), 2335-2338.
20. Gao, X.; Peng, L.; Li, H.; Chen, K., Formation of Humin and Alkyl Levulinate in the Acid-catalyzed Conversion of Biomass-derived Furfuryl Alcohol. Bioresources.com 2015, 10 (4).
21. Shirotori, M.; Nishimura, S.; Ebitani, K., One-pot synthesis of furfural derivatives from pentoses using solid acid and base catalysts. Catalysis Science & Technology 2014, 4 (4), 971-978.
22. Lehoux, R. R.; Bradt, C. B., Solid/fluid separation device and method for treating biomass including solid/fluid separation. Google Patents: 2014.
23. Benson, R. A. C.; Bradt, C.; Benech, R. O.; Lehoux, R. R., Cellulose pretreatment process. Google Patents: 2010.
24. Saleem, F.; Muller, P.; Eränen, K.; Warnå J.; Yu Murzin, D.; Salmi, T., Kinetics and modelling of furfural oxidation with hydrogen peroxide over a fibrous heterogeneous catalyst: effect of reaction parameters on yields of succinic acid. Journal of Chemical Technology & Biotechnology 2017, n/a-n/a.
25. Cai, C. M.; Zhang, T.; Kumar, R.; Wyman, C. E., Integrated furfural production as a renewable fuel and chemical platform from lignocellulosic biomass. Journal of Chemical Technology & Biotechnology 2014, 89 (1), 2-10.
26. Marcotullio, G.; De Jong, W., Chloride ions enhance furfural formation from d-xylose in dilute aqueous acidic solutions. Green Chemistry 2010, 12 (10), 1739-1746.
27. De Jong, W.; Marcotullio, G., Overview of biorefineries based on co-production of furfural, existing concepts and novel developments. International journal of chemical reactor engineering 2010, 8 (1).
28. British Pharmacopoeia. 2016; Vol. IV.
29. Olcay, H.; Subrahmanyam, A. V.; Xing, R.; Lajoie, J.; Dumesic, J. A.; Huber, G. W., Production of renewable petroleum refinery diesel and jet fuel feedstocks from hemicellulose sugar streams. Energy & Environmental Science 2013, 6 (1), 205-216.
30. Curtis, R. G.; Hatt, H. H., Equilibria In Furfural-Water Systems Under Increased Pressure And The Influence of Added Salts Upon The Mutual Solbilities of Furfural And Water. Australian Journal of Scientific Research, Series : A Physical Sciences 1948, 1, 213.
31. Hu, S.; Guan, Y.; Cai, D.; Li, S.; Qin, P.; Karim, M. N.; Tan, T., A novel method for furfural recovery via gas stripping assisted vapor permeation by a polydimethylsiloxane membrane. Scientific Reports 2015, 5, 9428.
32. Gupta, P.; Nanoti, A.; Garg, M. O.; Goswami, A. N., THE REMOVAL OF FURFURAL FROM WATER BY ADSORPTION WITH POLYMERIC RESINS. Separation Science and Technology 2001, 36 (13), 2835-2844.
33. Ghosh, U. K.; Pradhan, N. C.; Adhikari, B., Separation of furfural from aqueous solution by pervaporation using HTPB-based hydrophobic polyurethaneurea membranes. Desalination 2007, 208 (1), 146-158.
34. Haan, J. P., Process for separating furfural from a liquid aqueous phase comprising furfural and one or more organic acids. Google Patents: 2011.
35. Ray, M. S., Chemical Process Design, by R. Smith, McGraw-Hill, Inc., New York, USA (1995). 460 pages. ISBN 0-07-059220-9. Developments in Chemical Engineering and Mineral Processing 1995, 3 (1), 56-56.
36. Li, X.; Lan, X.; Wang, T., Selective oxidation of furfural in a bi-phasic system with homogeneous acid catalyst. Catalysis Today 2016, 276, 97-104.
37. GESTIS Succinic acid. http://gestis-en.itrust.de/nxt/gateway.dll/gestis_en/037700.xml?f=templates$fn=default.htm$3.0 (accessed March 05).

TABLE 1

Composition of the hemicellulose prehydrolysate used in this study.

| Component | Concentration (g/L) |
| --- | --- |
| Xylo-oligosaccharides | 52.30 |
| Xylose | 31.97 |
| Glucose | 2.11 |
| Arabinose | 3.18 |
| Acetic acid | 2.37 |
| Hydroxy methylfurfural | 1.02 |
| Furfural | 0.35 |

TABLE 2

The concentrations of xylose, furfural and humins obtained in the acid hydrolysis of prehydrolysate after 4 h using different acid concentrations.

|  | 1% acid hydrolysis | 1.5% acid hydrolysis | 2% acid hydrolysis | 2.5% acid hydrolysis | 10% acid hydrolysis | 10% acid hydrolysis in autoclave |
|---|---|---|---|---|---|---|
| Xylose (g/L) | 84.0 | 80.0 | 96.0 | 79.0 | 76.0 | 75.0 |
| Furfural (g/L) | 4.1 | 5.8 | 6.0 | 6.2 | 1.3 | 5.9 |
| Humins (g/L) | 2.7 | 4.8 | 6.6 | 7.8 | 33.3 | 33.2 |

The invention claimed is:

1. A method of synthesizing succinic acid comprising:
mixing a source of aqueous xylose with an organic solvent having low water solubility at a ratio of 1:1 to 1:5, wherein the organic solvent is selected from the group consisting of toluene, chloroform and ethyl acetate;
adding a suitable acid, thereby converting the xylose to furfural;
recovering an organic solvent phase comprising the furfural; and
adding hydrogen peroxide to the organic solvent phase comprising the furfural at a ratio of hydrogen peroxide to furfural of 1:1 to 1:5 in the presence of a macroreticular ion exchange catalyst having high acidic strength, said furfural transferring from the organic solvent phase to an aqueous phase comprising hydrogen peroxide and converting to succinic acid in the aqueous phase.

2. The method according to claim 1 wherein the organic solvent is toluene.

3. The method according to claim 1 wherein the source of xylose is a hemicellulose prehydrolysate.

4. The method according to claim 3 wherein the hemicellulose prehydrolysate is from sugarcane, rice husk, corn cob, wheat straw, an agriculture residue or a forest residue.

5. The method according to claim 1 wherein the hydrogen peroxide is added at a ratio of about 4 parts $H_2O_2$ to about 1 part furfural.

6. The method according to claim 1 wherein the macroreticular ion exchange catalyst having high acidic strength is a macroreticular polystyrene based ion exchange resin with strongly acidic sulfonic group.

7. The method according to claim 6 wherein the macroreticular ion exchange catalyst having high acidic strength is Amberlyst 15™ (macro reticular polystyrene based ion exchange resin with strongly acidic sulfonic group).

8. The method according to claim 1 wherein the suitable acid is sulfuric acid.

9. The method according to claim 8 wherein the sulfuric acid is added at 1-5% (w/w).

10. The method according to claim 1 wherein the xylose is converted to furfural at a temperature of about 100° C.

11. The method according to claim 10 wherein the xylose is converted to furfural at a temperature of about 100° C. for approximately 4-6 hours.

12. The method according to claim 11 wherein the toluene phase is cooled to room temperature before adding the hydrogen peroxide.

* * * * *